(12) United States Patent
Habecker

(10) Patent No.: US 6,482,236 B2
(45) Date of Patent: Nov. 19, 2002

(54) PROSTHETIC ANKLE JOINT MECHANISM

(75) Inventor: Matthew J. Habecker, 1580 Stoney Creek Dr., Charlottesville, VA (US) 22902

(73) Assignee: Matthew J. Habecker, Charlottesville, VA (US)

(*) Notice: Subject to any disclaimer, the term of this patent is extended or adjusted under 35 U.S.C. 154(b) by 0 days.

(21) Appl. No.: 09/974,121

(22) Filed: Oct. 9, 2001

(65) Prior Publication Data

US 2002/0045946 A1 Apr. 18, 2002

Related U.S. Application Data

(60) Provisional application No. 60/281,330, filed on Apr. 4, 2001, and provisional application No. 60/239,769, filed on Oct. 12, 2000.

(51) Int. Cl.⁷ .................................................. A61F 2/30
(52) U.S. Cl. ........................ 623/18.11; 623/53; 623/50
(58) Field of Search .............................. 623/52, 53, 47, 623/48, 49, 50, 38, 51, 54, 55, 39, 42, 43, 18.11

(56) References Cited

U.S. PATENT DOCUMENTS

| 4,506,395 | A |   | 3/1985  | Haupt           |
| 4,959,073 | A |   | 9/1990  | Merlette        |
| 5,156,630 | A | * | 10/1992 | Rappoport et al.|
| 5,766,264 | A | * | 6/1998  | Lundt           |
| 5,913,901 | A | * | 6/1999  | Lacroix         |
| 6,129,766 | A | * | 10/2000 | Johnson et al.  |
| 6,187,052 | B1| * | 2/2001  | Molino et al.   |

* cited by examiner

Primary Examiner—Pedro Philogene

(57) ABSTRACT

A prosthetic ankle joint consisting of an upper housing (1) and a lower housing (2) which are connected to and rotate about a shared axis (3). A plurality of motion members (5) are utilized to control the motion of the ankle joint through weight-bearing and non weight-bearing conditions. The presence or absence of an adjustable anterior element (12) and posterior element (13) will dictate the allowable relative motion of the lower housing to the upper housing. The upper receptacle (4) allows the ankle to be attached to a tube clamp adapter (15) and pylon (8). The lower receptacle (14) allows for the rigid attachment of a prosthetic foot (16).

19 Claims, 5 Drawing Sheets

PROSTHETIC ANKLE JOINT MECHANISM

CROSS-REFERENCE TO RELATED APPLICATION

This application claims the benefit of Provisional Patent Application Ser. Nos. 60/281,330 filed Apr. 4, 2001 and 60/239,769 filed Oct. 12, 2000.

BACKGROUND

1. Field of Invention

This invention relates to the field of prosthetics, specifically to prosthetic ankle joints.

2. Description of Prior Art

In the last 100 years, the field of prosthetics has experienced a slow evolution from being an anecdotal craft to a legitimate medical profession. As one might expect, the components used in the field have undergone an equal form of evolution as new science, theory and materials have entered the profession. Of the evolving mechanisms, the prosthetic ankle joint has assumed many different shapes, designs and compositions as the most accurate solution to a suitable prosthetic replacement for the lost human ankle has been sought.

Existing lower extremity prosthetic ankle/foot systems tend to simulate more than replicate the motions that a normal human ankle experiences throughout the gait cycle. In U.S. Pat. No. 4,506,395 to Haupt (1985), the motion of plantarflexion in a prosthetic system is simulated only by the compression of a low durometer foam in a prosthetic foot which manipulates weight line positions rather than kinematically accurate changes in foot position. U.S. Pat. No. 6,129,766 to Johnson, et al. (2000), discloses an ankle joint design which incorporates a set of bumpers to limit ankle motion. An additional design found in U.S. Pat. No. 4,959,073 to Merlette (1990), simulates ankle motion through the deformation of an entire foot and ankle segment.

There remains a terrific need for a prosthetic ankle joint that seeks to accurately replicate the function and timing of normal muscle activity throughout the gait cycle. Although existing designs may allow for some ankle motion for the prosthetic user, most of the foot/ankle components are very limited in their functional motion and adjustability and require greater than normal forces to actuate. There is no current foot/ankle system which allows its function to be fine tuned to each patient to maximize the normal motions experienced not only through the gait cycle, but through their general activities of daily living as well.

Previous prosthetic ankle designs also fall short of maximizing a patient's function because they do not allow for any critical angular adjustments to improve functional ankle control or to address indiviual alignment concerns. The design of most prosthetic ankles or foot/ankle combinations, also restricts the pt. from wearing a variety of different shoes with varying heel heights and usually limit the amputee to the use of one type of prosthetic foot.

SUMMARY

In accordance with the present invention a prosthetic ankle joint comprises an upper and lower housing that are joined by a common axis and manipulated in space by motion members as well as chamber elements within the upper housing.

OBJECTS AND ADVANTAGES

Accordingly, besides the objects and advantages of the prosthetic ankle joint described in my above patent, several objects and advantages of the present invention are:

a) To provide an ankle joint which provides the most accurate kinematic replication of foot and ankle relationships during the gait cycle.
b) To provide an ankle joint which allows functional foot motion for the patient in a seated or non-weight bearing position.
c) To provide an ankle joint whose plantarflexion activation threshold can be fine-tuned for different activities by the prosthetist or the user.
d) To provide an ankle joint that is fully adjustable to accommodate a variety of different shoe heel heights worn by the user.
e) To provide an ankle joint that can be aligned and adjusted by a prosthetist to maximize the performance of a selected prosthetic foot.
f) To provide an ankle joint which is adapted to fit a multitude of prosthetic feet.
g) To provide an ankle joint which replicates the height of a normal ankle joint.
h) To provide an ankle joint which ultimately limits the quadriceps demand at initial contact by significantly decreasing the knee flexion moment and increasing the plantarflexion response of the foot.
i) To provide an ankle joint which ultimately decreases the overall energy expenditure of the amputee through the implications of a more natural gait.
j) To provide an ankle joint which simulates the eccentric contractions of dorsiflexor muscles upon the foot at initial contact through the deformation of its motion members.
k) To provide an ankle joint which simulates the concentric action of plantarflexor muscles upon the foot during stance through the limitation of upper housing motion by the chamber elements.
l) To provide an ankle joint which simulates the concentric action of the dorsiflexor muscles upon the foot during swing phase through the open-chain response of its motion members.
m) To provide an ankle joint which is completely modular and can be attached to appropriate existing prosthetic componentry both proximal and distal to itself.
n) To provide an ankle joint which is narrow in form to allow for accurate medial-lateral dimensions to be maintained in a cosmetic covering.
o) To provide an ankle joint which has a minimum of moving parts for decreased maintenance requirements.
p) To provide an ankle joint which is resistant to moisture to provide an added degree of freedom to its user.
q) To provide an ankle joint which can be placed in the line of progression of its user to minimize harmful torques during ambulation.
r) To provide an ankle joint which can be cheaply manufactured and provided to a greater patient population due to its affordability.
s) To provide an ankle joint which is functionally appropriate for all existing levels and classifications of patient walking abilities.
t) To provide an ankle joint which has a minimum of components as to increase its ability to assume a lightweight form.

DRAWING FIGURES

Figure 1:
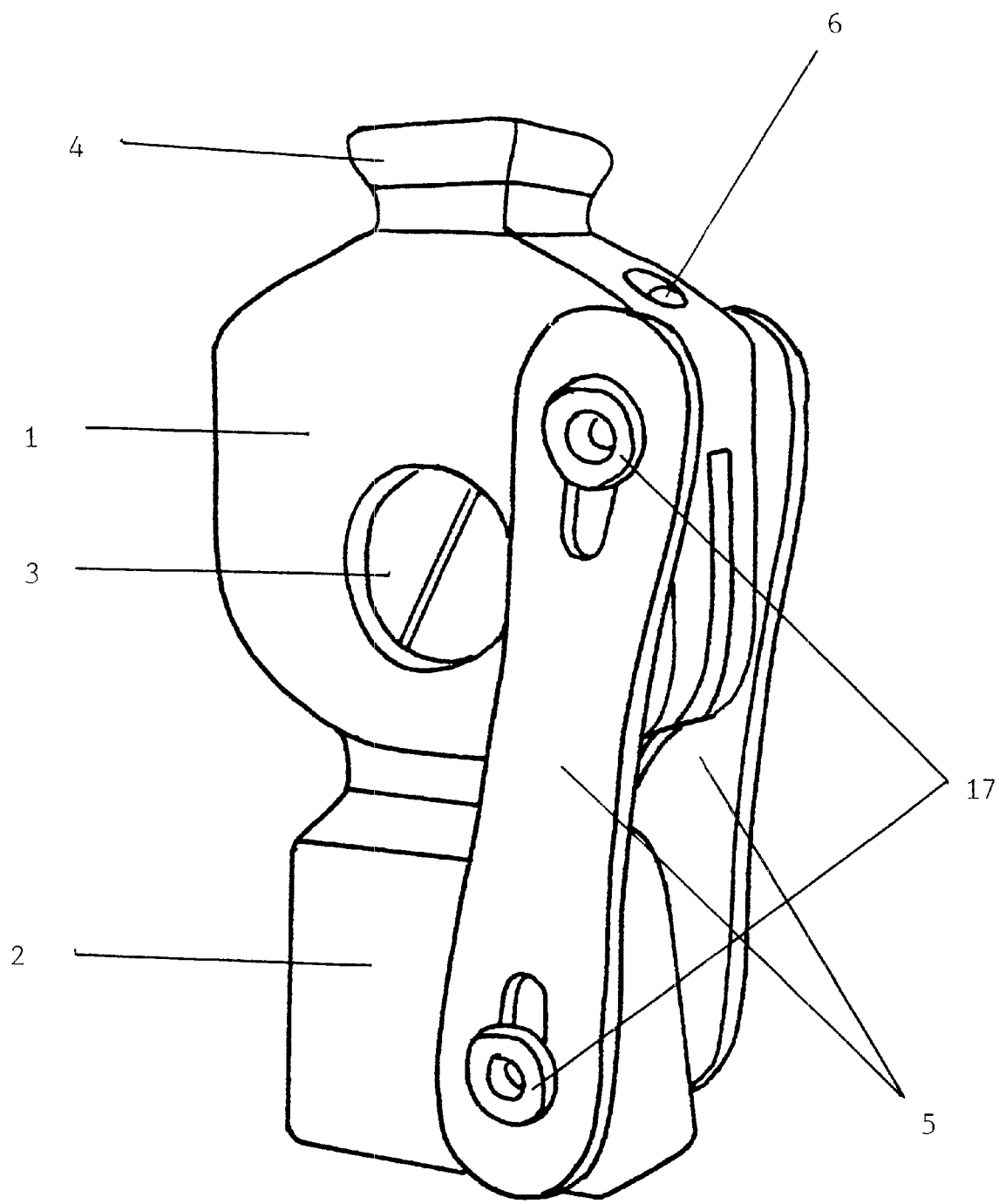
FIG. 1 is an isometric view of the prosthetic ankle joint.

REFERENCE NUMERALS IN DRAWINGS 1 upper housing
2 lower housing
3 axis
4 upper receptacle
5 motion member
6 chamber (anterior)
7 articular surface
8 pylon
9 chamber (posterior)
10 element retainer (anterior)
11 element retainer (posterior)
12 element (anterior)
13 element (posterior)
14 lower receptacle
15 tube clamp adapter
16 prosthetic foot
17 motion member attachment
18 foot bolt

DESCRIPTION-FIGS

Figure 2:
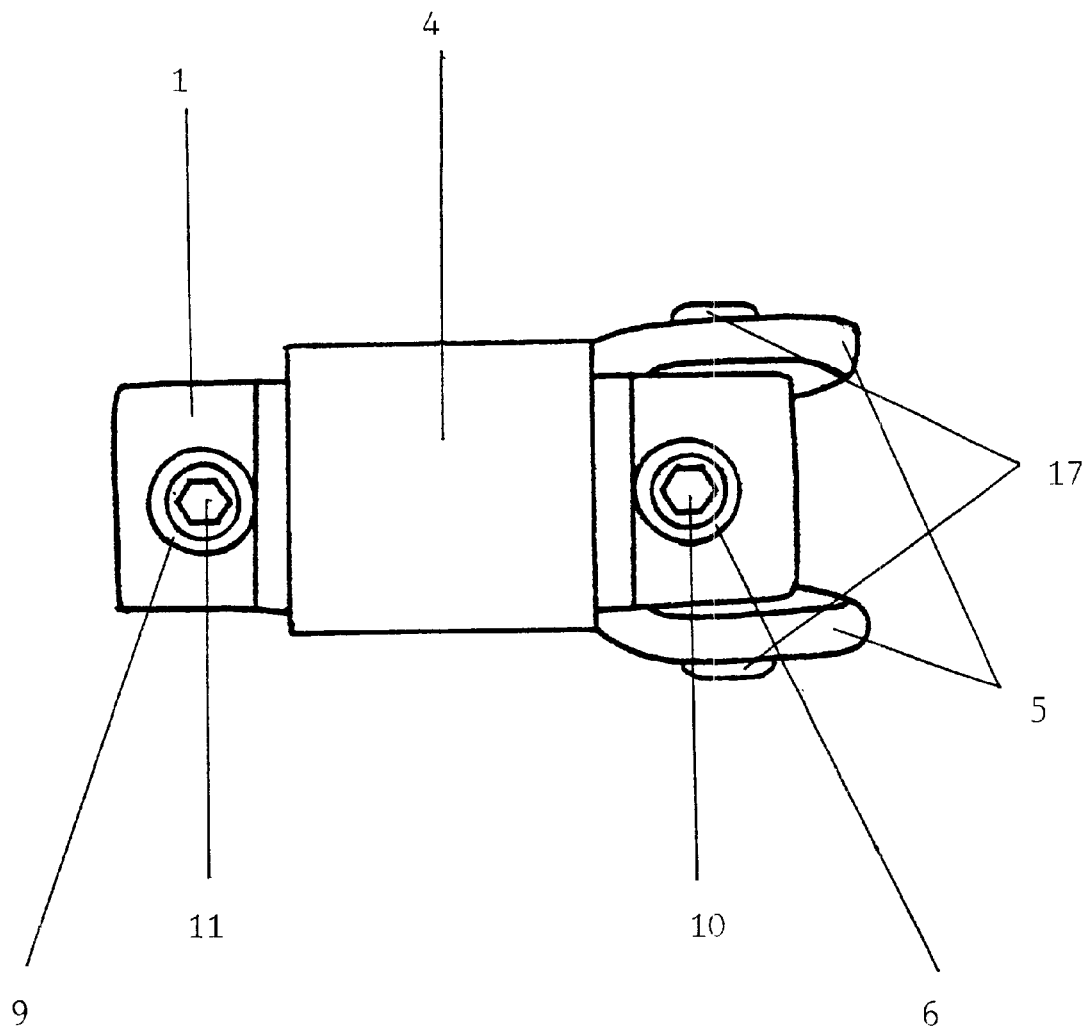
FIG. 2 is a top view of the prosthetic ankle joint.
Figure 3:
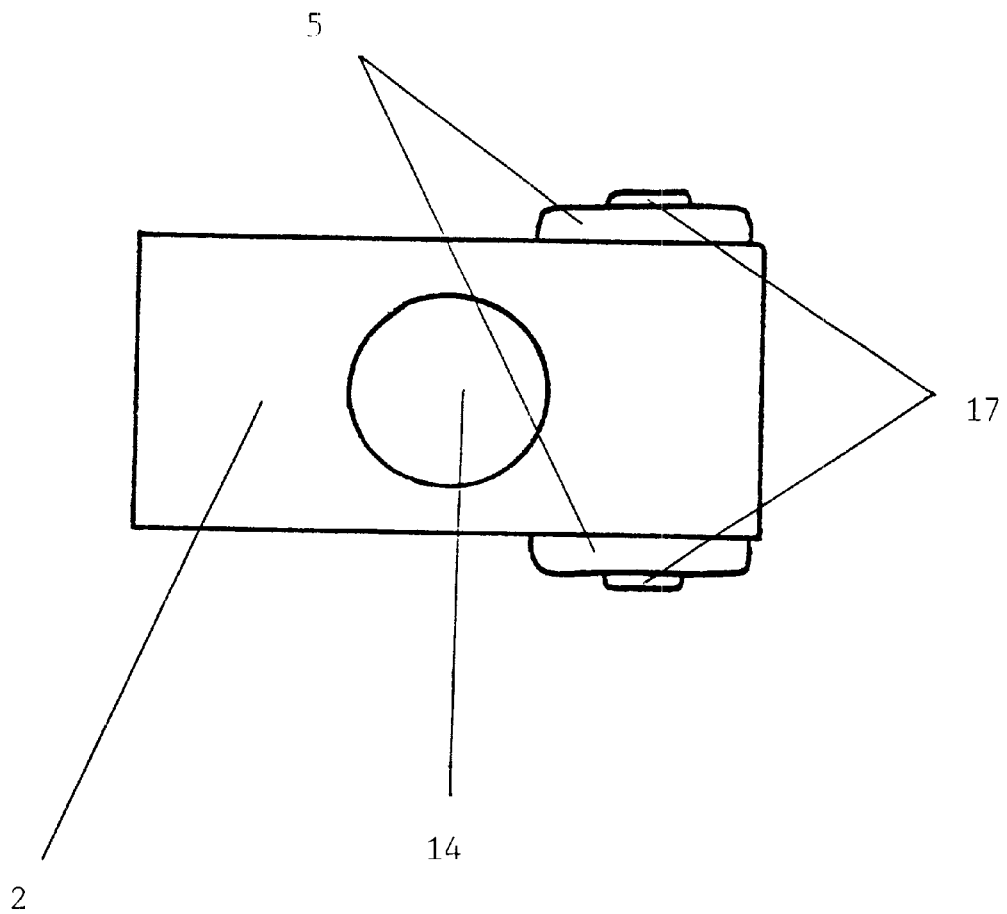
FIG. 3 is a bottom view of the prosthetic ankle joint.
Figure 4:
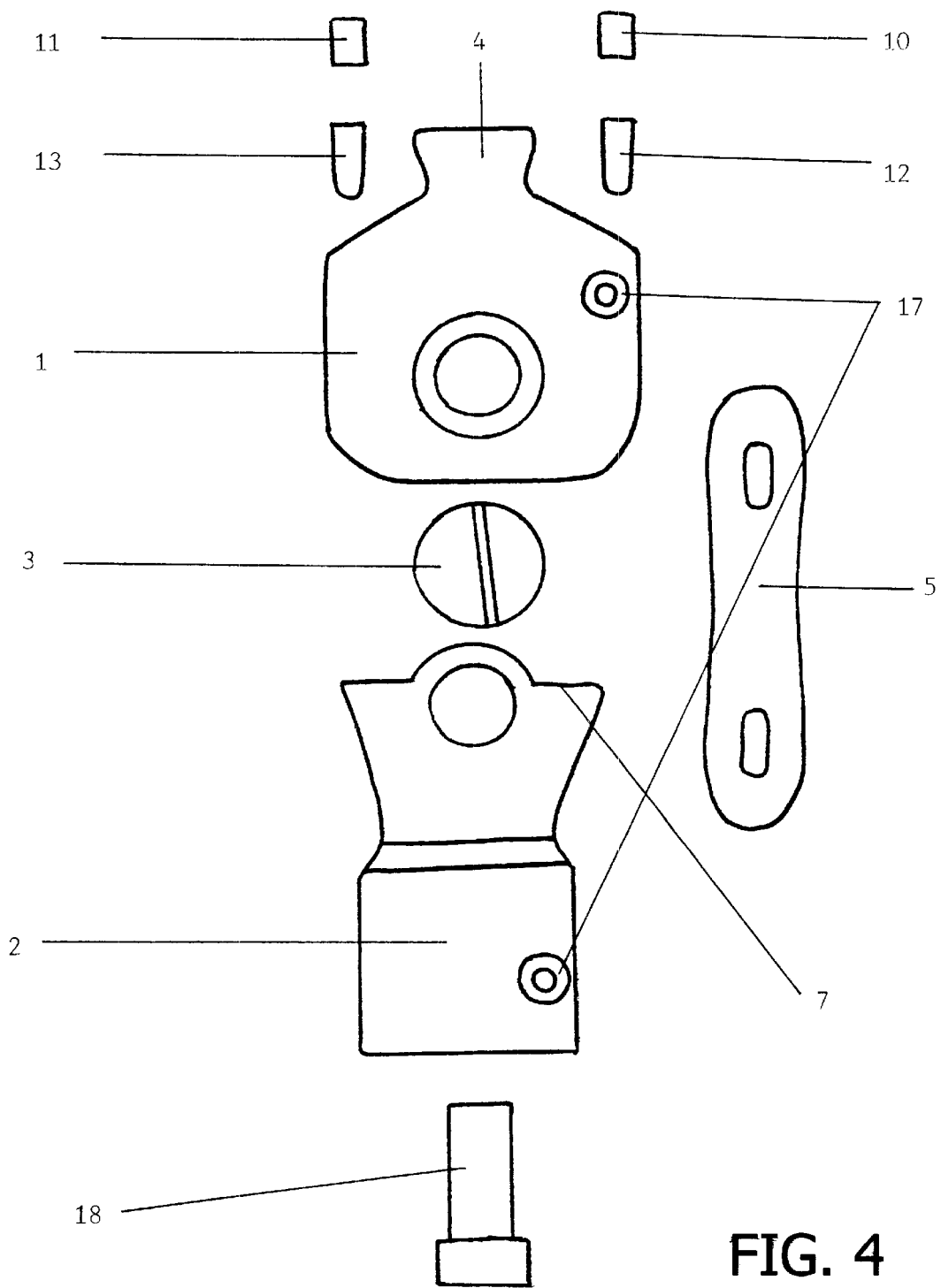
FIG. 4 is a side view of the prosthetic ankle joint with the upper and lower housings separated.
Figure 5:
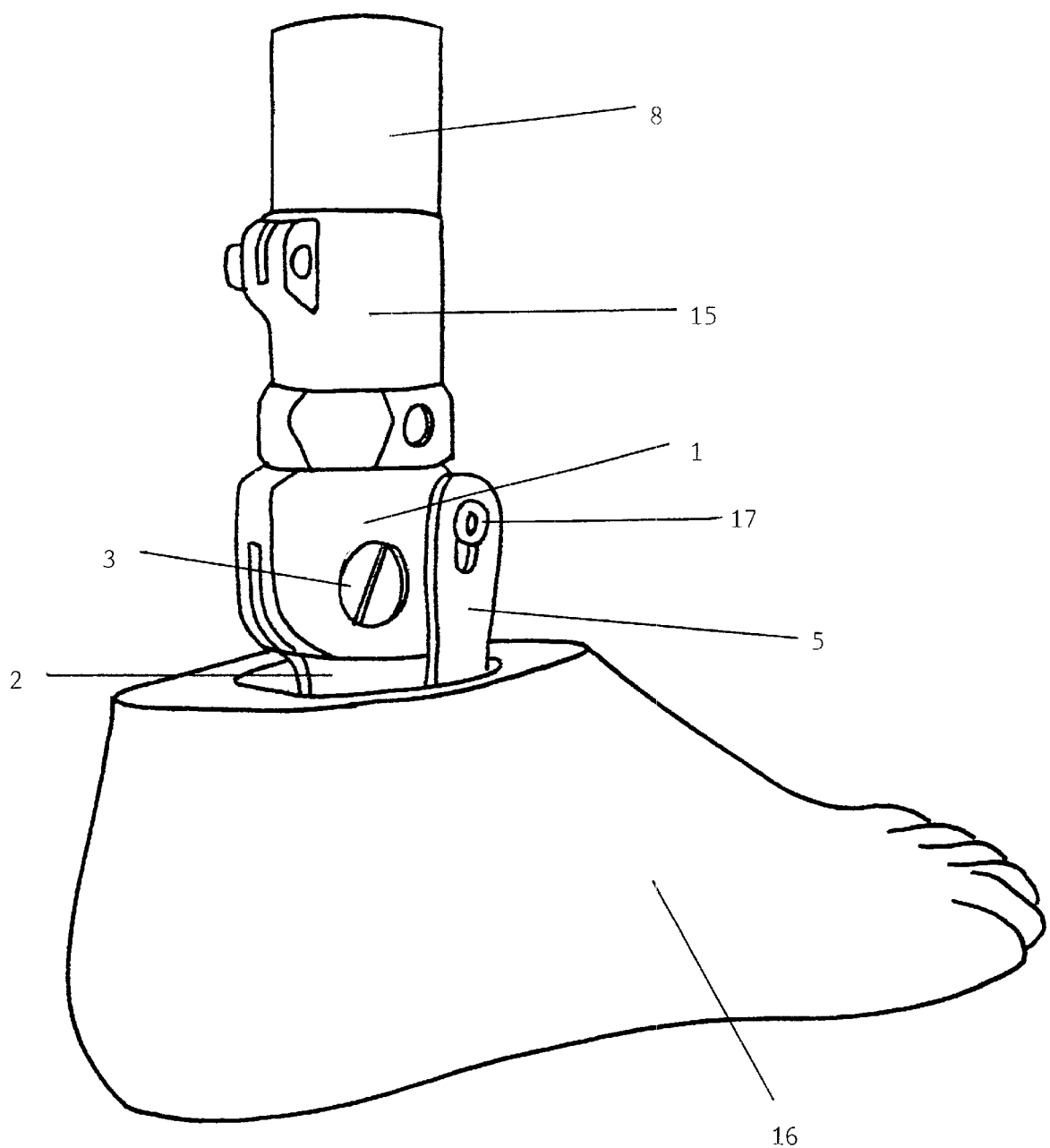
FIG. 5 is an isometric view of the prosthetic ankle joint with tube clamp adapter, pylon and foot attached.

A preferred embodiment of the prosthetic ankle joint is illustrated in FIGS. 1–4. In the preferred embodiment, the upper housing 1 and lower housing 2 would be comprised of a light-weight metal or composite, such as titanium or carbon fiber. The housings will be connected by an axis 3 which also allows free rotation. The anterior chamber 6 is located in front of the axis 3 and is directly positioned above the corresponding area of the articular surface 7 on the lower housing 2. Likewise, a posterior chamber 9 is located behind the axis and is positioned above the corresponding area of the same articular surface. An adjustable anterior element 12 and posterior element 13 can be placed within their respective chambers to act upon the articular surface. In the preferred embodiment, the anterior and posterior elements are rigid pins with a compressible material at the end in contact with the articular surface. However, the elements can be exchanged with springs, compressible material, ball bearings, or other types of pins which may be comprised of a myriad of different materials or combinations of different materials. The different elements are manipulated within the chambers by the respective anterior element retainer 10 and posterior element retainer 11. In the preferred embodiment, the element retainers are alien screws which are threaded into the chambers. However, the element retainers can consist of any other material that securely holds the chamber elements in their selected positions, such as, plastic, metal or composites. In addition, the element retainers can be shaped to be easily manipulated like a key by the user. The upper receptacle 4 is shaped to allow for attachment to an industry standard tube clamp adapter 15 and pylon 8.

The articular surface of the lower housing fits neatly within the upper housing and is shaped to be perpendicular to the elements acting upon it with the housings in a vertical alignment. However, the articular surface of the lower housing can be shaped in different ways to maximize its performance or to optimally contact the chamber elements if the chamber positions are relocated within the upper housing. In the preferred embodiment, the lower receptacle 14 is drilled to accept an industry standard foot bolt 18 which connects the prosthetic foot 16 to the ankle joint. However, the lower receptacle can be adapted to accept a compatible pyramid of a prosthetic foot that is similar to the upper receptacle previously described.

A motion member 5 can be seen spanning the ankle joint axis and held in place by way of a motion member attachment 17 at each of its ends. In the preferred embodiment, there are two motion members which are comprised of a highly elastic material. However, a number of different motion members can be attached to the ankle joint housings in different positions and may be comprised of materials with varying durometers and elastic properties.

ADVANTAGES

From the description above, a number of advantages of my prosthetic ankle joint become evident:

(a) Plantarflexion and dorsiflexion motion can be completely controlled by the elements placed in the anterior and posterior chambers.

(b) The ankle can be adjusted by the user to accommodate varying shoe heel heights.

(c) A selection of different motion means will allow for controlled plantarflexion at heel strike for patients of varying sizes and activity levels.

(d) A selection of different motion means will allow for control of dorsiflexion response during swing phase.

(e) With the addition of multiple motion means with varying durometers, a natural replication of muscle intensity at different stages of the gait cycle can be achieved.

(f) The modular and low profile design of the ankle maximize the number of components that may be used with the joint.

(g) The natural motion provided by the ankle joint will maximize a patient's stability during the gait cycle and therefore reduce their overall energy expenditure.

(h) The presence of a single axis joint will allow for more accurate gait studies to be performed due to its mechanical simplicity.

OPERATION—FIGS 1, 2, 3, 4, 5

The operation of the prosthetic ankle joint is based on weight-bearing and non-weight-bearing conditions. For descriptive purposes, it will be assumed that the right side of an amputee is being observed as he walks in a forward direction.

Upon heel strike, the prosthetic foot 16 plantarflexes toward the ground, causing the lower housing 2 to move in a clockwise motion relative to the upper housing 1. When the clockwise rotation of the lower housing is initiated, the relative distance increases between the shared motion member attachments 17 of any given motion member 5. With the increase in distance, the respective motion member will expand and provide resistance to the motion it is experiencing. The lower housing will continue to rotate in this direction until the articular surface 7 of the lower housing comes into contact with the previously positioned posterior element 13. Rotation may also be controlled by the resistance provided by the motion members in their expanded condition.

The use of multiple motion members may be integrated into the ankle design to provide varying amounts of resistance at different points in time. Once the prosthetic foot 16 has achieved a foot flat position, the upper housing will begin moving in a clockwise manner relative to the lower housing as the patient's body advances over the foot. The upper housing will continue to move in a clockwise direction until its anterior element 12 comes into contact with the articular surface of the lower housing. At this point in time, the ankle joint motion will be locked and the properties of the prosthetic foot will regulate all motion relative to the pylon 8. The motion members will also be restored to their originally positioned length at this point.

Following the toe off position of the foot in preparation for swing phase, the preset tension in the motion members is sufficient to hold the prosthetic ankle and foot in a dorsiflexed posture to prevent toe drag.

The position that the articular surface meets the posterior element is completely adjustable and can be set by turning the posterior element retainer. In a similar manner, the position that the articular surface meets the anterior element can be adjusted by turning the anterior element retainer. This manipulation is also useful for accommodating varying shoe heel heights.

CONCLUSION, RAMIFICATIONS AND SCOPE

Although previous designs have sought to employ the latest use of materials and technology, most have fallen short of addressing the most basic requirements for replicating normal ankle motion during all phases of the gait cycle and beyond. The current ankle design seeks to find a "happy medium" of plantarflexion at heel strike for individuals of differing weights and walking abilities at various cadences. In addition, the current ankle design seeks to allow its users to experience the ability to control the plantarflexion motion of their prosthetic foot in a seated position. Ideally, this motion may allow an amputee to functionally control the pedals of an automobile or simply tap their foot to a favorite song. Such function from existing ankle designs is simply unheard of. The current ankle design seeks to address the very important need of fine tuning the ankle motion for their activities of daily living and addresses the need for an ankle design that provides its user with functional abilities in a seated position.

Previous ankle design has followed the theory that plantarflexion response must be fairly rigid to control the phenomenon of "foot slap" that would otherwise be experienced at the "heel strike" phase of the gait cycle. Unfortunately, a rigid design, in the case of a below the knee amputee, promotes the premature flexion of the knee during early stance phase, which has been scientifically confirmed to drastically increase the user's energy expenditure. The current ankle design seeks to satisfy the delicate balance that would allow for the maximally allowable plantarflexion response at heel strike without its user experiencing the "foot slap", or the premature knee flexion previously described. Importantly, the elastic membranes utilized in the ankle's design seek to replicate the specific actions of normal muscle activity around the ankle at the appropriate times during the gait cycle. The replication of a more natural gait pattern, as one would expect, would ultimately reduce the energy expenditures of amputees wearing the ankle and positively affect their overall mobility and function.

The ankle also consists of a minimum number of parts and components which would allow for less expensive production costs. Ideally, the savings would be passed on to the medical community to make the cutting edge technology available to patients all over the world.

Although some descriptions and specificities have been provided above, these should not be construed as limiting the scope of the invention but as merely providing illustrations of some of the presently preferred embodiments of this invention. For example, the housings could assume a myriad of compositions and forms; the chambers and elements can have varying sizes, shapes and properties; the motion members can range in number, orientation and elasticity, etc.

Thus the scope of the invention should be determined by the appended claims and their legal equivalents, rather than by the examples given.

I claim:

1. A prosthetic ankle joint which replicates normal walking kinematics comprising:
    a female upper housing for joining to proximal prosthetic components;
    a male lower housing for joining to distal prosthetic components;
    anatomical joint axis replication means for approximating anatomical height and functional performance of a human ankle;
    adjustable heel height means for accommodating the heel heights of multiple shoes;
    eccentric dorsiflexor muscle simulation means for controlling immediate plantarflexion motion during stance phase;
    concentric dorsiflexor muscle simulation means for controlling plantarflexion motion during swing phase;
    individualized eccentric and concentric dorsiflexor muscle intensity simulation means for controlling plantarflexion motion during stance and swing phase;
    concentric plantarflexor muscle simulation and timing means for resisting stance phase dorisflexion;
    eccentric dorsiflexion muscle simulation and timing means for resisting stance phase plantarflexion;
    wherein plantarflexion and dorsiflexion motions of the prosthetic ankle joint replicate the normal kinematic performance of an anatomical ankle joint.

2. The prosthetic ankle joint of claim 1 wherein said upper housing comprises a substantially hollowed distal section, into which an anterior chamber and a posterior chamber exit.

3. The prosthetic ankle joint of claim 1 wherein said anterior chamber and said posterior chamber are wider than the hollowed distal section of said upper housing and are cylindrical and tapped.

4. The prosthetic ankle joint of claim 1 wherein said anterior chamber and said posterior chamber respectively house an anterior element and a posterior element.

5. The prosthetic ankle joint of claim 4 wherein said anterior element and said posterior element are rigid in nature, and contact respective anterior and posterior aspects of said lower housing at a predetermined range of motion.

6. The prosthetic ankle joint of claim 4 wherein said anterior element and said posterior element are adjusted within the respective said anterior chamber and said posterior chamber by a respective anterior element retainer and posterior element retainer.

7. The prosthetic ankle joint of claim 6 wherein the said anterior element retainer and said posterior element retainer are threaded and adjustable by hand.

8. The prosthetic ankle joint of claim 1 wherein said upper housing further comprises a sloping upper receptacle which tapers into a male inverted pyramid to accept industry standard female pyramidal adapters for connection to a prosthetic socket.

9. The prosthetic ankle joint of claim 1 wherein said lower housing further comprises a proximally extending arm which inserts into said upper housing.

10. The prosthetic ankle joint of claim 1 wherein said lower receptacle has a tapped lower receptacle for insertion of a threaded foot bolt as to rigidly connect a prosthetic foot.

11. The prosthetic ankle joint of claim 1 wherein said anatomical joint axis replication means is a single axis wherein an averaged anthropometrically accurate ankle axis height is maintained.

12. The prosthetic ankle joint of claim 1 wherein all plantarflexion and dorsiflexion motion are controlled by one or more user adjustable motion members, spanning said axis, which are pivotally connected to anterior aspects of said upper housing and said lower housing at their respective upper and lower ends by way of motion member attachments.

13. The prosthetic ankle joint of claim 12 wherein said motion members have elastic memory are stackable upon said motion member attachments, and exist in varying strengths.

14. The prosthetic ankle joint of claim 12 wherein said eccentric dorsiflexor muscle simulation means comprises said motion members, wherein the elongation of said motion members resists plantarflexion motion during stance phase.

15. The prosthteic ankle joint of claim 12 wherein said concentric dorsiflexor muscle simulation means comprises said motion members, wherein the contraction of said motion members resists plantarflexion motion during swing phase.

16. The prosthetic ankle joint of claim 12 wherein said individualized eccentric and concentric dorsiflexor muscle intensity simulation means comprise said motion members, wherein the number and strengths of said motion members utilized, determine the elastic resistance to ankle plantarflexion.

17. The prosthetic ankle joint of claim 1 wherein said concentric plantarflexor muscle simulation and timing means comprise said anterior element wherein said anterior element resists the motion of said lower housing into dorsiflexion.

18. The prosthetic ankle joint of claim 1 wherein said eccentric dorsiflexion muscle simulation and timing means comprise said posterior element wherein said posterior element resists the motion of said lower housing into plantarflexion.

19. The prosthetic ankle joint of claim 1 wherein said adjustable heel height means comprises said anterior element wherein said anterior element resists the motion of said lower housing into dorsiflexion.

* * * * *